United States Patent [19]
Lodin et al.

[11] Patent Number: 5,460,608
[45] Date of Patent: Oct. 24, 1995

[54] KINK FREE CATHETER

[75] Inventors: David W. Lodin, Maple Grove; Scott R. Smith, Chaska, both of Minn.

[73] Assignee: SCIMED Life Systems, Inc., Maple Grove, Minn.

[21] Appl. No.: 186,805

[22] Filed: Jan. 25, 1994

[51] Int. Cl.⁶ ............................................. A61M 25/00
[52] U.S. Cl. .................... 604/96; 604/282; 606/194
[58] Field of Search .................... 604/96, 280, 282; 606/192, 194

[56] References Cited

U.S. PATENT DOCUMENTS

| | | | |
|---|---|---|---|
| 3,832,253 | 8/1974 | DiPalma et al. | 156/86 |
| 3,865,666 | 2/1975 | Shoney | 156/245 |
| 3,884,242 | 5/1975 | Bazell et al. | 128/351 |
| 3,985,601 | 10/1976 | Panagrossi | 156/229 |
| 4,276,874 | 7/1981 | Wolvek et al. | 128/1 D |
| 4,307,722 | 12/1981 | Evans | 128/344 |
| 4,323,071 | 4/1982 | Simpson et al. | 128/343 |
| 4,385,635 | 5/1983 | Ruiz | 128/658 |
| 4,563,181 | 1/1986 | Wijayarathna et al. | 604/280 |
| 4,571,240 | 2/1986 | Samson et al. | 604/96 |
| 4,581,390 | 4/1986 | Flynn | 523/112 |
| 4,597,755 | 7/1986 | Samson et al. | 604/96 |
| 4,638,805 | 1/1987 | Powell | 128/344 |
| 4,646,719 | 3/1987 | Neuman et al. | 128/1 D |
| 4,723,936 | 2/1988 | Buchbinder et al. | 604/95 |
| 4,729,384 | 3/1988 | Bazenet | 128/691 |
| 4,782,834 | 11/1988 | Maguire et al. | 128/344 |
| 4,807,626 | 2/1989 | McGirr | 128/328 |
| 4,808,164 | 2/1989 | Hess | 604/95 |
| 4,813,934 | 3/1989 | Engelson et al. | 604/99 |
| 4,848,805 | 7/1989 | Sos et al. | 128/344 |
| 4,917,666 | 4/1990 | Solar et al. | 604/95 |
| 4,927,413 | 5/1990 | Hess | 604/95 |
| 4,960,410 | 10/1990 | Pinchuk | 604/96 |
| 4,981,478 | 1/1991 | Evard et al. | 604/282 |
| 4,990,143 | 2/1991 | Sheridan | 604/282 |
| 4,994,032 | 2/1991 | Sugiyama et al. | 604/96 |
| 5,019,057 | 5/1991 | Truckai | 604/282 |
| 5,069,674 | 12/1991 | Fearnot et al. | 604/282 |
| 5,125,895 | 6/1992 | Buchbinder et al. | 604/95 |
| 5,190,520 | 3/1993 | Fenton, Jr. et al. | 604/43 |
| 5,195,971 | 3/1993 | Sirhan | 604/96 |
| 5,195,991 | 3/1993 | Pike | 604/282 |
| 5,250,069 | 10/1993 | Nobuyoshi et al. | 606/192 |
| 5,324,259 | 6/1994 | Taylor et al. | 604/96 |
| 5,342,386 | 8/1994 | Trotta | 604/96 X |
| 5,380,304 | 1/1995 | Parker | 604/282 |

FOREIGN PATENT DOCUMENTS

| | | |
|---|---|---|
| 0254885 | 2/1988 | European Pat. Off. . |
| 0349640B1 | 7/1994 | European Pat. Off. . |
| WO89/08473 | 9/1989 | WIPO . |
| WO93/05842 | 4/1993 | WIPO . |

OTHER PUBLICATIONS

Press Release by Medtronic, Inc., dated Aug. 6, 1990, announcing the approved commercial release of 18K catheter for coronary balloon angioplasty.

Press Release by Medtronic, Inc., dated Aug. 19, 1993, announcing its new Spirit (TM) balloon catheter for coronary angioplasty.

*Primary Examiner*—John D. Yasko
*Attorney, Agent, or Firm*—Robert Atkinson; John Rissman; Luke Dohmen

[57] ABSTRACT

A balloon catheter having an outer shaft and an inner shaft in which the inner shaft is constructed to protect itself over its entire length and especially in its most vulnerable areas without adversely effecting its flexibility, trackability, or pushability or the catheter's deflation time. The inner shaft can be reinforced to prevent it from collapsing or breaking throughout its length and also improving the deflation time of the balloon.

5 Claims, 2 Drawing Sheets

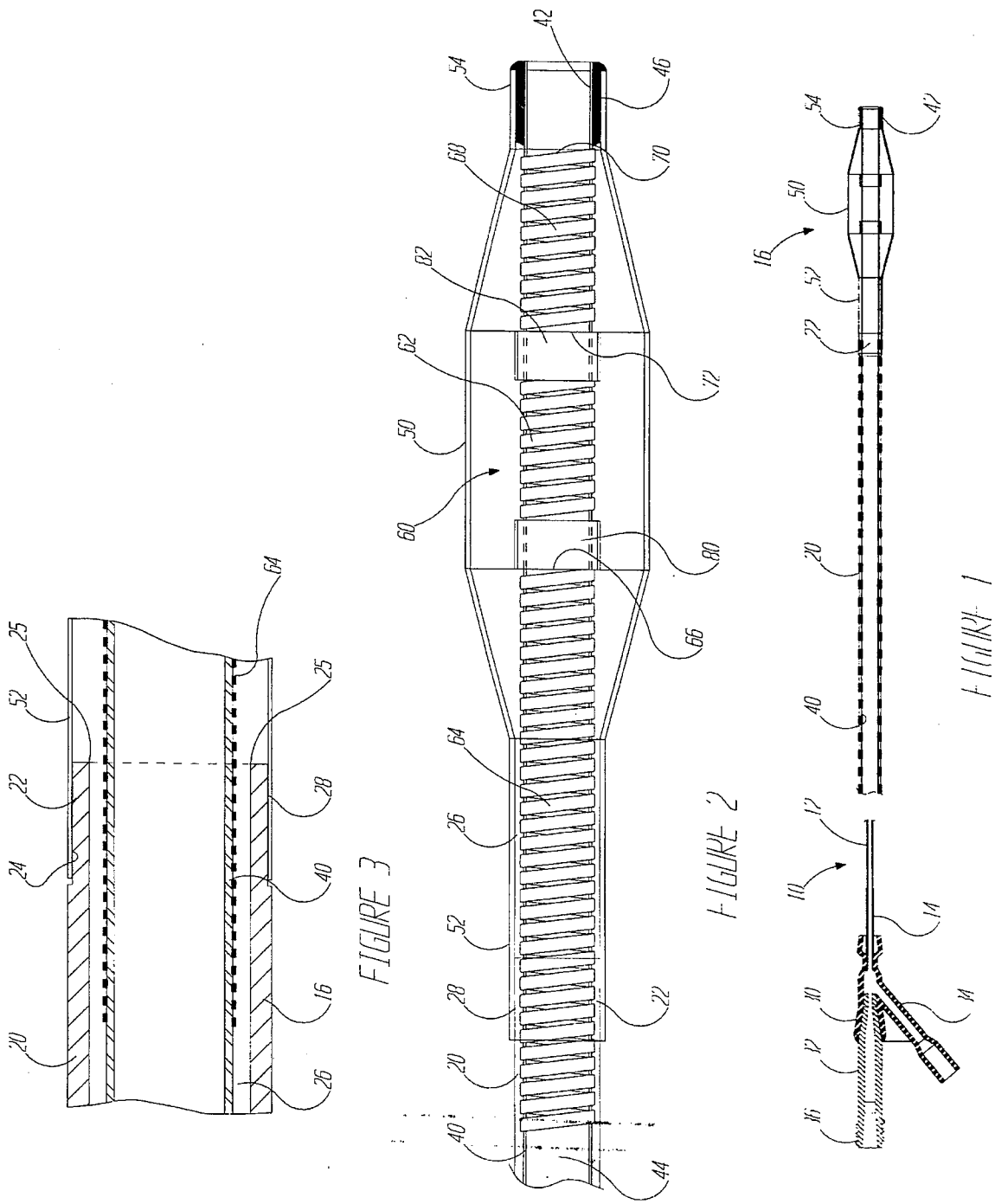

KINK FREE CATHETER

BACKGROUND OF THE INVENTION

The present invention relates to an intravascular catheter. In particular, the present invention relates to an intravascular catheter for use in percutaneous transluminal angioplasty (PTA) in large peripheral vessels, for example the legs and kidneys, that have an inside diameter in the range of 4–8 mm.

Angioplasty procedures have gained wide acceptance in recent years as an efficient and effective method for treating various types of vascular disease, particularly percutaneous transluminal coronary angioplasty (PTCA). The most widely used form of angioplasty makes use of a dilatation catheter which has an inflatable balloon at its distal end. The catheter is percutaneously inserted into the patient's vascular system and is maneuvered from its proximal end through the vascular system. The physician uses a fluoroscope to guide the dilatation catheter through the vascular system until the un-inflated balloon is positioned across the stenosis. The catheter should be sufficiently flexible to flex around the acute bends that it encounters along the vascular system. The balloon is then inflated by supplying fluid under pressure, through an inflation-deflation lumen, to the balloon. Inflation of the balloon causes the vessel lumen to increase in diameter and thus reestablish acceptable blood flow through the vessel.

It can become necessary, during an angioplasty procedure, to quickly deflate and or remove the balloon catheter. For this reason it is important that the inflation-deflation lumen of the catheter be of sufficient size to permit rapid deflation of the balloon. In addition to the major factors, size and geometry of the inflation-deflation lumen, the walls of the inflation-deflation lumen should have a low resistance to fluid flow.

Catheters for use in PTA and PTCA have undergone a continuous evolution over the past 20 years particularly insofar as certain physical characteristics. There has been a continuing effort to reduce the profile or shaft size of dilatation catheters, so that the catheter can not only reach but also extend across a very tight stenosis. The profile or shaft size as well as the wall thickness of both the inner and outer shaft have been reduced in an effort to minimize the profile.

One of the most widely used angioplasty catheters is referred to as a "coaxial-over-the-wire" catheter. A coaxial-over-the-wire catheter is one in which a separate guide wire lumen is provided in the catheter so that a guide wire can be used to establish the path through the vascular system. The dilatation catheter can then be advanced over the guide wire until the balloon carried by the catheter is positioned across the stenosis. The guide wire lumen in a conventional coaxial-over-the-wire catheter is defined by an inner shaft that extends beyond the distal end of the catheter outer shaft. The proximal end of the balloon is secured to the outer distal end of the outer shaft. The distal end of the balloon is secured to the outer surface of the inner shaft. As a result of this conventional construction, both the inner and outer shafts are coextensive for all but the balloon area of the catheter. Both the inner and outer shafts of an over-the-wire catheter contribute to its "trackability" and "pushability." However, the outer shaft terminates short of the balloon area of the catheter and in this area the outer shaft does not function to support the thin walled inner shaft. In "coaxial-over-the-wire" catheters, the inside diameter of the inner shaft should be slightly larger than the outer diameter of the guide wire to permit the catheter to freely slide along the guide wire. Thus the outer diameter of the guide wire establishes the inner diameter of the inner shaft. In current catheters the inner shaft typically has a very thin wall thickness. Thus for a catheter having a given profile, the very thin inner shaft wall thickness establishes a maximum for the cross sectional area of the annulus shaped lumen between the inner and outer shaft. In catheters of this type the annulus shaped lumen, defined by the outer surface of the inner shaft and the inner surface of the outer shaft, functions as the inflation-deflation lumen. The cross sectional area of this annulus shaped lumen is the major factor in establishing the deflation time of the balloon. It is apparent that to increase the cross-sectional area of this lumen, in a catheter having a fixed profile or outer diameter, the wall thickness of the inner and or outer shafts must be decreased.

Dilation catheters must be sufficiently flexible to pass through tight curves or radii in the vascular system. The ability of a catheter to bend and advance through the vascular system is commonly referred to as trackability of the catheter. Thin shaft sections improve the trackability of a balloon catheter, however, if the walls become too thin, the tube sections tend to kink, collapse or burst. The resistance to kinking, collapsing or bursting can be increased by incorporating into a catheter shaft a coil spring in which the turns are spaced from each other so as to not compromise flexibility of the catheter. The inner shaft should have the ability to withstand being crushed by the pressure of the inflation fluid when the balloon is inflated and other mechanical pressures that it is exposed to, such as the uninflated balloon being wrapped around it for insertion purposes. The inner shaft is exposed to some of these mechanical forces at a time when the guide wire is not extending through the inner lumen and thus must rely on its own structure to resist such outside forces. The inner lumen must be maintained when the guide wire is not extending through it to enable the physician to perform distal dye injections and distal pressure measurements."

As catheters are being advanced through the vascular system they must be flexed to follow the sharp bends that are encountered in the vascular system. The un-inflated balloon is wrapped around the inner shaft, such that there are several layers of balloon material wrapped around the inner shaft during the catheter insertion procedure. The balloon material is stiff and thus has a tendency to kink or buckle. When the balloon area of the catheter is being advanced through a sharp bend, there is a risk that the inner surface of the un-inflated and folded balloon will engage the outer surface of the thin walled inner shaft. Such engagement could kink or collapse the thin walled inner shaft causing it to engage the guide wire within the inner shaft and resist or prevent advancement of the catheter along the guide wire. The possibility of the thin inner shaft kinking in the balloon area increases with larger balloon diameters. Although the wall thickness of the balloon is very thin, as the balloon diameters increase, the total amount of material contained in the balloon increases dramatically.

U.S. Pat. No. 4,994,032 discloses a vascular catheter including a "coaxial-over-the-wire" embodiment in which the inner and outer shafts are formed of flexible material including polyolefins, such as polyethylene, polypropylene, ethylene-propylene copolymers or ethylene-vinyl acetate copolymers, thermoplastic resins, such as polyvinyl chloride, polyamide elastomers or polyurethane, silicone rubber or latex rubber. The distal end of the inner shaft extends beyond the distal end of the outer shaft and a balloon is secured to the distal end portions of both the inner and the outer shafts. A reinforcement is wound about a portion of the outer surface of the inner shaft in the area enclosed within the balloon to thus render this section of the inner shaft more resistance against buckling and or breaking. The reinforcement is made from a coiled wire formed of an X-ray opaque material to aid in obtaining a clear fluoroscopy image. The catheter disclosed in this patent provides for a reinforcement member in the vulnerable balloon area of the catheter, however the reinforcement disclosed in this patent does not protect the inner shaft in the area immediately below the distal end of the outer shaft. This unprotected area immediately below the distal end of the outer shaft is the most vulnerable area of the inner shaft and becomes even more vulnerable when the reinforcement disclosed in the '032 patent is utilized. When the catheter is bent while negotiating an acute bend in the blood vessel, the inner shaft engages the inner corner of the distal edge of the outer shaft. When this occurs the inner corner of the distal edge acts as a fulcrum about which the inner shaft bends. With all the pressure concentrated at this location the inner shaft is very vulnerable to collapsing or breaking at this point.

It is not sufficient to provide reinforcement only to the most vulnerable areas of the catheter if other areas of the catheter are also vulnerable. The catheter should have acceptable trackability and should be supported along its entire length such that it has the ability to be bent around tight radii without collapsing or kinking. In some catheters such protection against collapsing can be accomplished by integrating a reinforcing coil, that is constructed such that its turns are not in contact with each other, along the entire length of the inner shaft and in other catheters such a coil with spaces between the turns need only extend across the balloon area. Also the reinforcing coil need not be continuous and can function satisfactorily if separated into separated sections. This should be accomplished without violating the profile requirements and the internal lumen size requirements. Thus there is a need for a catheter of a given profile that has equivalent mechanical integrity as current catheters of the same profile but which is constructed of inner and outer shafts that have a combined wall thickness that is less than that of current catheters.

SUMMARY OF THE INVENTION

The present invention is directed to a catheter that protects the inner shaft against collapsing over its entire length and especially in its most vulnerable area without adversely effecting its flexibility, trackability or the catheter's deflation time. According to the invention, the apparatus comprises an outer shaft having a proximal and a distal end, an inner shaft having a proximal and a distal end, a balloon secured at one end to the distal end of the outer shaft and at the other end to the distal end of the inner shaft, and reinforcing means secured to the inner shaft that will reduce the likelihood of the inner shaft from collapsing or breaking throughout its length without decreasing the deflation time of the balloon.

The present invention is directed to an intravascular catheter which may be advanced over a guide wire, such as a dilation balloon catheter having a guide wire lumen extending the entire length of the catheter. The catheter includes a relatively stiff outer shaft that has a uniform cross section over its entire length and a relatively thin walled inner shaft which has a uniform cross section over its entire length. The lumen defined by the thin walled inner shaft functions as the guide wire lumen. The thin walled inner shaft extends beyond the distal end of the outer shaft and the balloon is secured to the distal ends of the outer and inner shafts. Thus, in the balloon area the relatively stiff outer shaft is not present to support the thin walled inner shaft. The distal portion of the thin walled inner shaft is reinforced by a kink resisting coil the turns of which do not contact each other thus leaving a space between the turns. The reinforced portion of the inner shaft underlies the balloon and extends across the junction between the proximal end of the balloon and the distal end of the outer shaft such that the catheter has a relatively flexible distal end and further closure or kinking of the thin walled inner shaft in the balloon area including its juncture with the outer shaft is prevented or reduced. The space between the turns of the coil allows the distal end of the catheter to remain flexible.

The resistance to collapsing of applicant's catheter, especially in the balloon area, has been greatly enhanced by the combination of the thin walled inner shaft and the kink resisting coils.

A primary object of this invention to provide a new catheter construction such that a catheter of a specific overall diameter will have equivalent mechanical integrity as current catheters of the same specific overall diameter but will have less wall thickness.

It is also an object of the present invention to provide a coaxial-over-the-wire type balloon catheter including a kink resisting coil in the balloon area that functions to protect the thin walled inner shaft and the juncture of the balloon to the outer shaft and will not create an impediment to rapid deflation of the balloon.

It is still another object of the present invention to provide a balloon catheter that resists kinking along its entire length and will permit rapid deflation of the balloon.

These and other objects and advantages of the present invention will no doubt become apparent to those skilled in the art after having read the following detailed description of the preferred embodiment which is contained in and illustrated by the various drawing figures.

BRIEF DESCRIPTION OF THE DRAWINGS

FIG. 1 is a cross sectional side view of the catheter in which the distal end is shown in a larger scale than the proximal end.

FIG. 2 is a cross sectional side view of the balloon area of the catheter.

FIG. 3 is an enlarged cross sectional side view of the juncture between the distal end of the outer shaft and the proximal end of the balloon.

DETAILED DESCRIPTION OF THE PREFERRED EMBODIMENT

Figure 4:
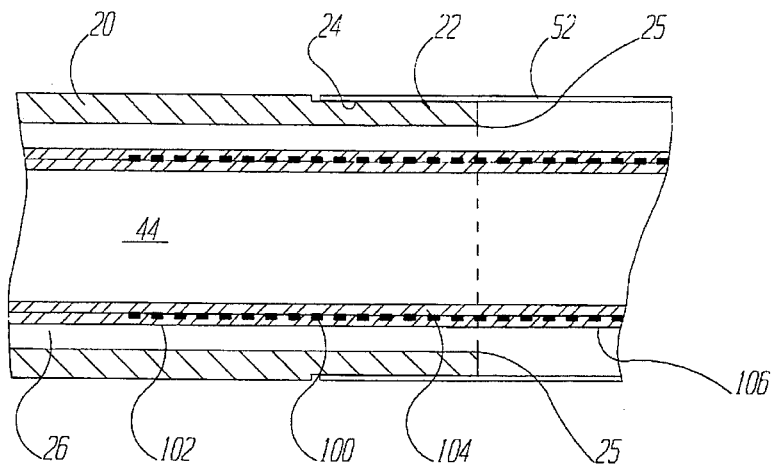
FIG. 4 is a cross sectional side view of another embodiment of applicant's catheter.

FIG. 1 is a cross sectional side view of the peripheral catheter 10 in which the manifold 30 and a section of the coaxial shaft 12 are shown in a relatively small scale and the distal end of the peripheral catheter 10 which includes the balloon 50 are shown in a larger scale.

Peripheral catheter 10 is comprised of a coaxial shaft 12 having a proximal end 14 and a distal end 16, and a balloon 50. The proximal end of peripheral catheter 10 is connected to the distal end of a manifold 30, which has a straight port 32 and a side port 34. The preferred embodiment of the peripheral catheter 10 has a working length of about 75 centimeters.

The coaxial shaft 12 includes an outer shaft 20 and an inner shaft 40. The lumen 44 formed by inner shaft 40 functions as the guide wire lumen. The annulus shaped lumen 26 defined by the outer surface of inner shaft 40 and the inner surface of outer shaft 20 functions as the inflation-deflation lumen for balloon 50. The proximal end 14 of coaxial shaft 12 extends into the distal end of the manifold 30 such that a guide wire extending through lumen 44 can exit the manifold 30 through the proximal end of straight port 32. A luer lock connection 36 is provided at the proximal end of straight port 32 to which a valve device including a hemo stasis seal, for example, a Tuohy-Borst type valve, can be connected. The hemo stasis seal functions to prevent blood loss through lumen 44. A syringe can be connected to the side port 34 of the manifold 30 for supplying inflation fluid to the balloon 50 through annulus shaped lumen 26.

The balloon 50 has a proximal end 52 that is secured to the distal end 22 of outer shaft 20 and a distal end 54 that is secured to the distal end 42 of the inner shaft 40.

Referring now to the preferred embodiment shown in FIGS. 2 and 3. FIG. 2 shows the balloon area of the peripheral catheter 10 in a larger scale than shown in FIG. 1, and FIG. 3 shows the juncture of the outer shaft 20 and the balloon 50 in a larger scale than shown in FIG. 2.

Outer shaft 20 is made of a thermoplastic material such as polyethylene having a relatively thick wall thickness, for example a wall thickness of about 0.006 inches. The outer surface of outer shaft 20 is provided with a silicone coating which enhances the trackability, pushability and the general usability of the peripheral catheter 10. The outer shaft 20 has a recessed portion 24 formed in its outer surface at its distal end 22. In the preferred embodiment of the peripheral catheter, the outer shaft 20 has an outside diameter of 5 French (about 0.0645 inches) throughout its length.

Inner shaft 40 is a thin walled tube made of thermoplastic material such as a polyethylene having a wall thickness of about 0.0027 inches plus or minus 0.00025 inches. In the preferred embodiment of the peripheral catheter 10 the inner shaft 40 has an inside diameter of about 0.0385 inches which is compatible with a 0.035 inch guide wire.

In the preferred embodiment of the peripheral catheter 10, the balloon 50 is made of low IV polyethylene terephthalate homopolyesters (PET) material and has a wall thickness of about 0.0007 inches. Balloon 50 has a proximal end 52 that is secured by urethane adhesive 28 to the recessed portion 24 of outer shaft 20. The distal end 54 of balloon 50 is secured by urethane adhesive 46 to the outer surface of inner shaft 40 at its distal end 42.

A stainless steel coil 60 is secured to the outer surface of inner shaft 40 in the balloon area of the peripheral catheter 10. The coil 60 is divided into three separate sections, a central section 62, a proximal section 64 and a distal section 68. The coil 60 has a proximal edge or outer proximal edge 66 at the end of its proximal section 64 that is adjacent to the central coil section 62. The coil 60 has a distal edge or outer distal edge 72 at the end of its distal coil section 68 that is adjacent to the central coil section 62. Distal coil section 68 has a distal end 70.

A proximal marker band 80, made for example of tantalum, is secured to the outer surface of inner shaft 40 between the proximal edge 66 of the coil 50 and the central coil section 62. A distal marker band 82, also made for example of tantalum, is secured to the outer surface of inner shaft 40 between the distal edge 72 of coil 60 and the central coil section 62. The marker bands 80 and 82 of the preferred embodiment have a wall thickness of about 0.002 inches.

The stainless steel coil 60 and the marker bands 80 and 82 are secured to the outer surface of inner shaft 40 by a coating of urethane adhesive. It should be noted that the turns of the coil are not in engagement with each other and there is always a space between adjacent turns of the coil. This is important to insure that shaft 40 retains its flexibility.

Referring now especially to FIG. 3, the relationship between the distal end 22 of the outer shaft 20, the proximal end 52 of balloon 50, the thin walled inner shaft 40 and the coil 60 will be discussed. A recessed portion 24 is formed in the outer surface of outer shaft 20 at its distal end 22 of a depth that the proximal end 52 of balloon 50 can be secured by adhesive 28 to the recessed portion and the outer diameter of the outer shaft 20 at this juncture remains unchanged from its preceding portion. It should be noted that when balloon 50 is un-inflated and folded, its diameter throughout the balloon area is substantially the same as or slightly larger than the outer diameter of outer shaft 20. As the peripheral catheter 10 is being manipulated through the patient's vascular system it must bend and twist. It is apparent in FIG. 3 that when the peripheral catheter is bent at the juncture of the outer shaft 20 with the balloon 50, the inside corner 25 of outer shaft 20 will tend to engage the outer surface of inner shaft 40. As a result, the inner shaft 40 is subjected to repeated contact by inside corner 25 and is vulnerable to being severed or crushed against the guide wire within inner shaft 40. The presence of the kink resisting coil 60 at this vulnerable area provides protection to the thin wall inner shaft 40 and reduces the possibility of its rupture or kinking. The coil 60 extends past the inside distal edge 25 in the proximal direction such that it underlies the recessed portion 24 of the outer shaft 20 and in so doing protects the adhesive securement of the proximal end of balloon 50 to the distal end 22 of outer shaft 20. Thus by extending the proximal end of coil 60 across the juncture of outer shaft 20 and balloon 50 both the inner shaft 40 and the adhesive juncture are protected.

In the preferred embodiment the material from which the outer shaft 20 and inner shaft 40 are constructed and the chosen wall thickness provides the catheter with acceptable stiffness and flexibility characteristics throughout. Also, in the preferred embodiment, the cross sectional area of the annulus shaped lumen 26 is of a size that will permit rapid deflation of the balloon 50. Although the annulus shaped lumen 26 is diminished in size somewhat in the area immediately proximal to the balloon area, since this diminished size area is relatively short it has virtually no adverse affect on the fluid flow through lumen 26. Thus, the preferred embodiment catheter provides superior mechanical integrity to a conventional catheter having the same profile and wall thickness.

Referring now to FIG. 4 which shows another embodiment of applicant's invention. FIG. 4 is similar to FIG. 3 and the same reference numbers are used to identify components that are identical. In this embodiment a reinforcement member 100 extends the entire length of inner shaft 40. Reinforcement member 100 is in the form of a helical coil formed from a material such as stainless steel. The reinforcement member 100 is enveloped between a first 102 and a second 104 shaft segment. The second shaft segment 104 has been shrunk such that it fills the void between adjacent spirals of the helical reinforcement member 100. The outer surface 106 of second shaft segment 104 has a smooth cylindrical shape, which is conducive to unimpeded fluid flow through annulus shaped lumen 26. The inner surface of first shaft segment 102 also has a smooth cylindrical shape and thus allows a guide wire free and unimpeded passage through lumen 44. The wall thickness of inner shaft 40 can be less than the wall thickness of a current catheter having the same profile and yet provide the same or better mechanical integrity of a catheter having a corresponding profile. This decreased wall thickness makes it possible to increase the cross section area of the annulus shaped lumen 26 which increases the deflation time. The inner shaft 40 can be fabricated by extruding the first shaft segment 102, applying the reinforcement member 100 to the outer surface of first shaft segment 102 and then extruding the second shaft segment 104 over the first shaft segment 102 and reinforcement member 100. The second shaft segment 104 could be shrunk during extrusion or in a later process. This embodiment provides a catheter that has superior mechanical integrity to a current catheter of equal profile.

Figure 5:
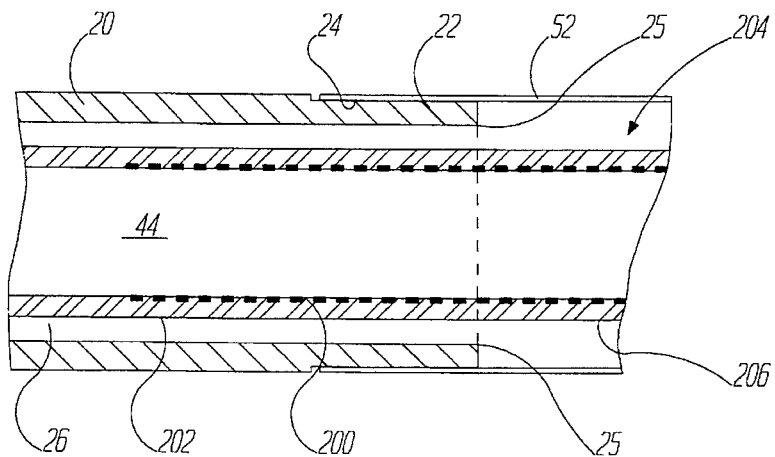
FIG. 5 is a cross sectional side view of another embodiment of applicant's catheter.

Referring now to FIG. 5 which shows another embodiment of applicant's invention. FIG. 5 is similar to FIG. 3 and the same reference numbers are used to identify corresponding components parts. In this embodiment a reinforcement member 200 extends the entire length of inner shaft 204. Reinforcement member 200 is in the form of a helical coil formed from a material such as stainless steel. The reinforcement member 200 is embedded into the inner surface 202 of inner shaft 204 such that the inner shaft fills the void between adjacent spirals of the helical shaped reinforcement member 200 and the inner surface 202 of inner shaft 204 has a smooth cylindrical surface. The outer surface 206 of inner shaft 204 has a smooth cylindrical shape, which is conducive to unimpeded fluid flow through annulus shaped lumen 26. The smooth cylindrical shape inner surface 202 allows a guide wire free and unimpeded passage through lumen 44. The wall thickness of inner shaft 204 can be less than the wall thickness of current catheters having the same profile and yet provide the same or better mechanical integrity. This decreased wall thickness makes it possible to increase the cross section area of the annulus shaped lumen 26 which increases the deflation time. The inner shaft 204 can be fabricated by extruding a tube of material over the coiled reinforcement member 200. The mandril onto which the inner shaft 204 is extruded has a smooth outer surface upon which the reinforcement member 200 is wrapped. Thus, this embodiment provides a catheter that has superior mechanical integrity as compared to a current catheter having equal profiles.

Figure 6:
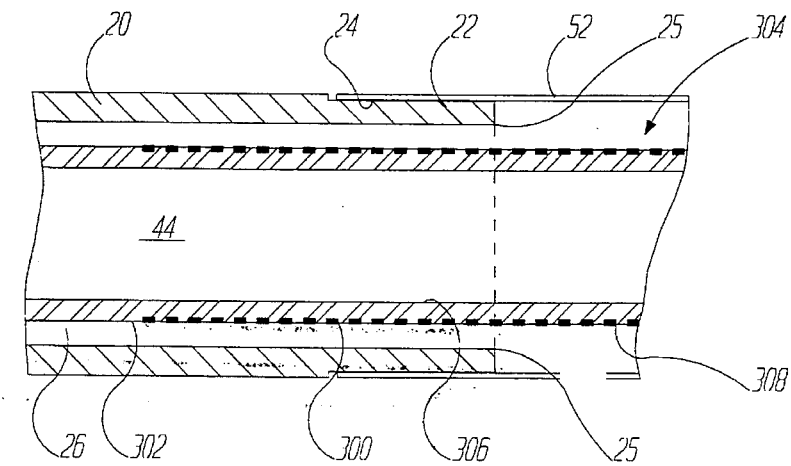
FIG. 6 is a cross sectional side view of another embodiment of applicant's catheter.

Referring now to FIG. 6 which shows another embodiment of applicant's invention. FIG. 6 is similar to FIG. 3 and the same reference numbers are used to identify corresponding components parts. In this embodiment a reinforcement member 300 extends the entire length of inner shaft 304. Reinforcement member 300 is in the form of a helical coil formed from a material such as stainless steel. The reinforcement member 300 is embedded into the outer surface 302 of inner shaft 304 such that the inner shaft fills the void between adjacent spirals of the helical shaped reinforcement member 300 and the inner surface 306 of inner shaft 304 has a smooth cylindrical surface. The outer surface 308 of inner shaft 304 has a smooth cylindrical shape, which is conducive to unimpeded fluid flow through annulus shaped lumen 26. The smooth cylindrical shape inner surface 306 allows a guide wire free and unimpeded passage through lumen 44. The wall thickness of inner shaft 304 can be less than the wall thickness of current catheters having the same profile and yet provide the same or better mechanical integrity. This decreased wall thickness makes it possible to increase the cross section area of the annulus shaped lumen 26 which increases the deflation time. The inner shaft 304 can be fabricated by extruding a tube of material and wrapping the reinforcement member 300 around the newly extruded strip. Thus, this embodiment provides a catheter that has superior mechanical integrity than a current catheter of equal profile.

Although the present invention has been described in terms of specific embodiments, it is anticipated that alterations and modifications thereof will no doubt become apparent to those skilled in the art. It is therefore intended that the following claims be interpreted as covering all such alterations and modifications that fall within the true spirit and scope of the invention.

What is claimed is:

1. A balloon catheter comprising:
    an outer thermoplastic shaft having a uniform wall thickness and proximal and distal ends,
    an inner thermoplastic shaft having a uniform wall thickness and proximal and distal ends, the inner surface of said inner thermoplastic shaft being smooth and unencumbered and defining a lumen having a given cross section area,
    the diameters and wall thickness of said outer and inner thermoplastic shafts being such that an annular shaped lumen of a given cross section area is formed between the inner surface of the outer thermoplastic shaft and the outer surface of the inner thermoplastic shaft,
    the distal end of the inner shaft being distal of the distal end of the outer shaft,
    a balloon having a proximal and a distal end,
    the proximal end of the balloon being bonded to the distal end of the outer shaft,
    the distal end of the balloon being bonded to the distal end of the inner shaft,
    said inner thermoplastic shaft including a reinforcing member extending axially therethrough, the reinforcing member being formed by a single layer of metallic wire in a helical pattern with a pitch greater than the width of the wire.

2. The invention as set forth in claim 1 in which said reinforcing member extends without interruption throughout the entire length of said inner thermoplastic shaft.

3. The invention as set forth in claim 2 in which said reinforcing member is made from a material such as stainless steel.

4. The invention as set forth in claim 2 in which a radiopaque marker is secured to the outer surface of the inner shaft such that it underlies said balloon.

5. The invention as set forth in claim 2 in which said reinforcing member extends through the center of the wall of the inner thermoplastic shaft such that the reinforcing member is not a part of the inner or outer surfaces of said inner thermoplastic shaft.

* * * * *